United States Patent [19]

Kato et al.

[11] Patent Number: 5,607,920
[45] Date of Patent: Mar. 4, 1997

[54] CONCANAVALIN A BINDING PROTEINS AND A 76KD CHONDROCYTE MEMBRANE PROTEIN (CMP) FROM CHONDROCYTES AND METHODS FOR OBTAINING SAME

[75] Inventors: Yukio Kato, Hiroshima; Haiou Pan, Tokorozawa; Kazuyuki Doi, Tokyo, all of Japan

[73] Assignee: Hoechst Japan Limited, Tokyo, Japan

[21] Appl. No.: 278,617

[22] Filed: Jul. 21, 1994

[30] Foreign Application Priority Data

Jul. 23, 1993 [JP] Japan .................................. 5-182338

[51] Int. Cl.$^6$ .............................. A61K 38/00; C07K 1/00; C12N 9/00
[52] U.S. Cl. .................................. 514/13; 514/8; 514/15; 530/395; 530/396; 530/412; 530/413; 530/427; 530/840; 435/183; 435/207
[58] Field of Search .................................. 514/13, 8, 15; 530/395, 396, 412, 413, 427, 840; 424/130.1, 139.1; 435/183, 207

[56] References Cited

U.S. PATENT DOCUMENTS 4,919,931  4/1990  Rosenberg née Göldner ........... 414/95

FOREIGN PATENT DOCUMENTS

0473080A2  3/1992  European Pat. Off. .

OTHER PUBLICATIONS

Yan et al, *The Journal of Biological Chemistry*, vol. 265, No. 17, pp. 10125–10131, Jun. 15, 1990.
Kato et al, *Japanese Journal of Bone Metabolism*, vol. 10, No. 2, pp. 187–192, 1992.
Kato et al, *The Journal of Cell Biology*, vol. 100, pp. 477–485, 1985.
Von der Mark et al, *Chemical Abstracts*, vol. 112, p. 269, Ref. #18590 h, 1990 (Ger. Offen. DE 3,721,790, Jan. 12, 1989).
Ben et al, *Chemical Abstracts*, vol. 110, p. 458, Ref. No. 112 181f, 1989 (Shika Kira Igakkai Zasshi 1988, 30(5) 703–6).
See et al, *Biochem J*, vol. 271, pp. 147–155, 1990.
Garratt et al.; A molecular model for the tumor–associated antigen, p. 97, suggests a Zn–binding function; FEBS Letters, vol. 305, No. 1 Jun. 1992; pp. 55–61.
Kato et al.; Sulfated Proteoglycan Synthesis by Confluent Cultures of Rabbit Costal Chondrocytes Grown in Presence of Fibroblast Growth Factor; The Journal of Cell Biology; vol. 100, 1985, pp. 477–485.
Yan et al.; Stimulation by Concanavalin A of Cartilage–Matrix Proteoglycan Synthesis in Chondrocyte Cultures; The Journal of Biological Chemistry; vol. 265, No. 17, Jun. 15, 1990, pp. 10125–10131.
Benya et al; Modulation of the Rabbit Chondrocyte Phenotype by Retinoic Acid Terminates Type II Collagen Synthesis Without Inducing Type I Collagen: The Modulated Phenotype Differs from that Produced by Subculture; Developmental Biology; vol. 118, 1986, pp. 296–305.
Kato et al.; Japanese Journal of Bone Metabolism; vol. 10, No. 2, 1992, pp. 187–192.

*Primary Examiner*—Howard E. Schain
*Assistant Examiner*—Abdel A. Mohamed
*Attorney, Agent, or Firm*—Finnegan, Henderson, Farabow, Garrett & Dunner, L.L.P.

[57] ABSTRACT

The invention is directed to purified and isolated concanavalin A-binding proteins from chondrocytes that are not present in dedifferentiated cells from chondrocytes. The invention is also directed to a purified and isolated chondrocyte membrane protein, (CMP), which is a concanavalin A-binding protein, with a molecular weight of about 76 kD in SDS-PAGE. After treatment with endoglycosidase, CMP has an apparent molecular weight of about 67 kD. The N-terminal amino acid sequence and several internal amino acid sequences are given for CMP. These proteins can be used in assays, methods, or treatments involving differentiation of chondrocytes and the control of cartilaginous osteogenesis.

8 Claims, 2 Drawing Sheets

CONCANAVALIN A BINDING PROTEINS AND A 76KD CHONDROCYTE MEMBRANE PROTEIN (CMP) FROM CHONDROCYTES AND METHODS FOR OBTAINING SAME

BACKGROUND AND SUMMARY OF THE INVENTION

The present invention relates to a novel glycoprotein which may participate in differentiation of chondrocytes. The new glycoprotein according to this invention may be also applied as a marker for differentiation of chondrocytes.

Animal cartilage tissues are composed of chondrocytes and matrices. Cartilage tissues constitute a major portion of skeleton during the embryonic stage and, after birth, they are replaced by bone through cartilaginous osteogenesis. At the onset of cartilaginous osteogenesis, cartilage tissues would be transformed from quiescent cartilage tissues to proliferative cartilage tissues and successively differentiated to hypertrophic cartilage tissues. As discussed above, it has been well-known that chondrocytes are essential cells particularly for osteogenesis during the growth period. However, there remain many aspects not yet elucidated in regard to differentiation of chondrocytes and cartilaginous osteogenesis.

On the other hand, Yan et al. [Yan et al.; J. Biol. Chem. vol. 265, pages 10125–10131, 1990)]and Kato et al. [Kato et al., Japanese Journal of Bone Metabolism, vol. 10, No. 2, pages 187–192 (1992)]have studied the effect of lectin on differentiation and proliferation of chondrocytes, and, inter alia, elucidated that concanavalin A, which is a jack bean lectin and has an affinity to α-D-mannose residues and α-D-glucose residues, can strongly increase synthesis of proteoglycan, which is a marker of differentiation of chondrocytes. There remain, however, many unclear points of its mechanism, wherein what receptor molecules concanavalin A may be bound to on the cell membrane of chondrocytes, how its stimulus may be transferred to such target sites as the nucleus in the cells and so on.

Moreover, it has been reported that chondrocytes, when excess retinoic acid (identical with Vitamin A) is added, may be modified to the so-called dedifferentiated type of cells, wherein they may be deformed in morphology from the spherical cells peculiar to differentiated chondrocytes to the fibroblast-like flat, expanded cellular form with an increased expansibility and may biochemically lose a synthesis ability of glicosaminoglycan (GAG), which is a differentiation marker for chondrocytes and other [Benya et al., Develop. Biol., vol. 118, pages 296–305 (1986)]. However, there has not yet been reported any relationship between the reactivity of chondrocytes to concanavalin A and the differentiation of chondrocytes.

Hence the problem of the present invention was to elucidate the substance capable of controlling the function of chondrocytes and, in the end, the substance capable of controlling enhancement of osteogenesis and to elucidate the substance relating to the differentiation of chondrocytes. This substance leads to a new type of therapy, prophylaxis and diagnosis of cartilaginous metabolic diseases and/or metabolic bone diseases.

In order to solve the above-mentioned problem, the present inventors have attempted to obtain a new membrane glycoprotein on the chondrocyte membrane bound to concanavalin A having a potent differentiation-enhancing activity to chondrocytes. And further, the present inventors have also elucidated a relationship between the protein thus obtained and the differentiation of chondrocytes by comparative tests with dedifferentiated cells having no more properties peculiar to chondrocytes with retinoic acid added.

Hence the present invention refers to a concanavalin A-binding protein (CMP) existing in chondrocytes, but not in dedifferentiated cells from chondrocytes. In a preferred embodiment CMP has a molecular weight of about 76 KD or of about 67 KD after treatment endoglycosidase as analyzed by SDS-PAGE. In a further particularly preferred embodiment CMP contains at least the N-terminal amino acid sequence SEQ ID NO:1:
    Ser Val Glu Val Arg Xaa Xaa Thr Ala Ser Glu Pro Pro Gln Gln
    1             5             10           15 or at least one of the internal sequences:

SEQ ID NO:2:
    His Thr Thr Tyr Phe Asp Asn Thr Asn Gly His Asn Pro Glu Pro Xaa
    1             5             10           15

Ala Ala

SEQ ID NO:3:
    Thr Val Gly Trp Asn Val Pro Val Gly Tyr Leu Val Asp Ser Gly Arg
    1             5             10           15

SEQ ID NO:4:
    Thr Thr Tyr Gln Asp Thr Leu Gly Pro Asp Tyr Val Ala Ala Leu Glu
    1             5             10           15

Gly Xaa Gln Ser
                20

SEQ ID NO:5:
    Tyr Tyr Asp Tyr Ser Gly Ala Phe Arg
    1             5 wherein Xaa means an unknown amino acid.

CMP can be obtained by a method containing the following steps:

(a) isolating chondrocytes;

(b) separating membrane proteins from the chondrocytes of step (a);

(c) isolating concanavalin A-binding glycoproteins through a concanavalin A-affinity column; and (d) isolating CMP, preferably by a method wherein prior to step (c) other membrane proteins than concanavalin A-binding glycoproteins were separated.

Most preferred, CMP can be isolated by the following method:

As to the materials for chondrocytes, one may use cartilaginous tissues of various animals and one may obtain chondrocytes, for example, by treatment of the material of costal cartilage growth plates of rabbits with protease and collagenase according to the method by Kato et al. [Kato et al., J. Cell Biol., vol. 100, pages 477–485 (1985,)]. The chondrocytes thus separated can be incubated in a medium containing fetal calf serum (FCS) in petri plates at 37° C. under environment of 5% $CO_2$ and 95% air. The chondrocytes thus incubated can be recovered, fractioned by means of a homogenizer and subjected e.g. to precipitation equilibrium centrifugation with sucrose equilibrium density-gradients of 17%/40% in order to recover membrane proteins. The membrane proteins thus recovered can be developed directly with a concanavalin A-affinity column or in a preferred embodiment previously developed with an affinity column using, for example, a representative lectin, a wheat germ lectin for removing other membrane proteins bound to lectins than concanavalin A and thereafter developed with a concanavalin A-affinity column, or using other methods to further fractionate concanavalin A-binding protein fractions. Dedifferentiated cartilage cells are derived and formed with various concentrations of retinoic acids and concanavalin A-binding protein fractions are also fractionated. The specificity of the concanavalin A-binding proteins thus obtained to cartilage cells can be investigated by comparing these fractions by way of SDS-polyacrylamide gel electrophoresis (SDS-PAGE). SDS-Page analysis of the deglycosilated forms of CMP was also carried out. The glycoprotein specific to the aimed cartilage cells was characterized by amino acid sequencing of the N-terminus.

CMP provided according to this invention is the substance that relates to differentiation of chondrocytes and also to control of functions by chondrocytes and control of cartilaginous osteogenesis. Therefore, CMP or antibodis against CMP can be utilized as a new type of therapy, prophylaxis and diagnosis against cartilaginous metabolic diseases and/or metabolic bone diseases. Therefore, the present invention refers also to a pharmaceutical or a diagnostic aid containing CMP or antibodis against CMP.

The present invention will be explained in detail by way of the following examples, which are not to be construed to limit the present invention.

DESCRIPTION OF PREFERRED EMBODIMENTS

Example 1

Figure 1:
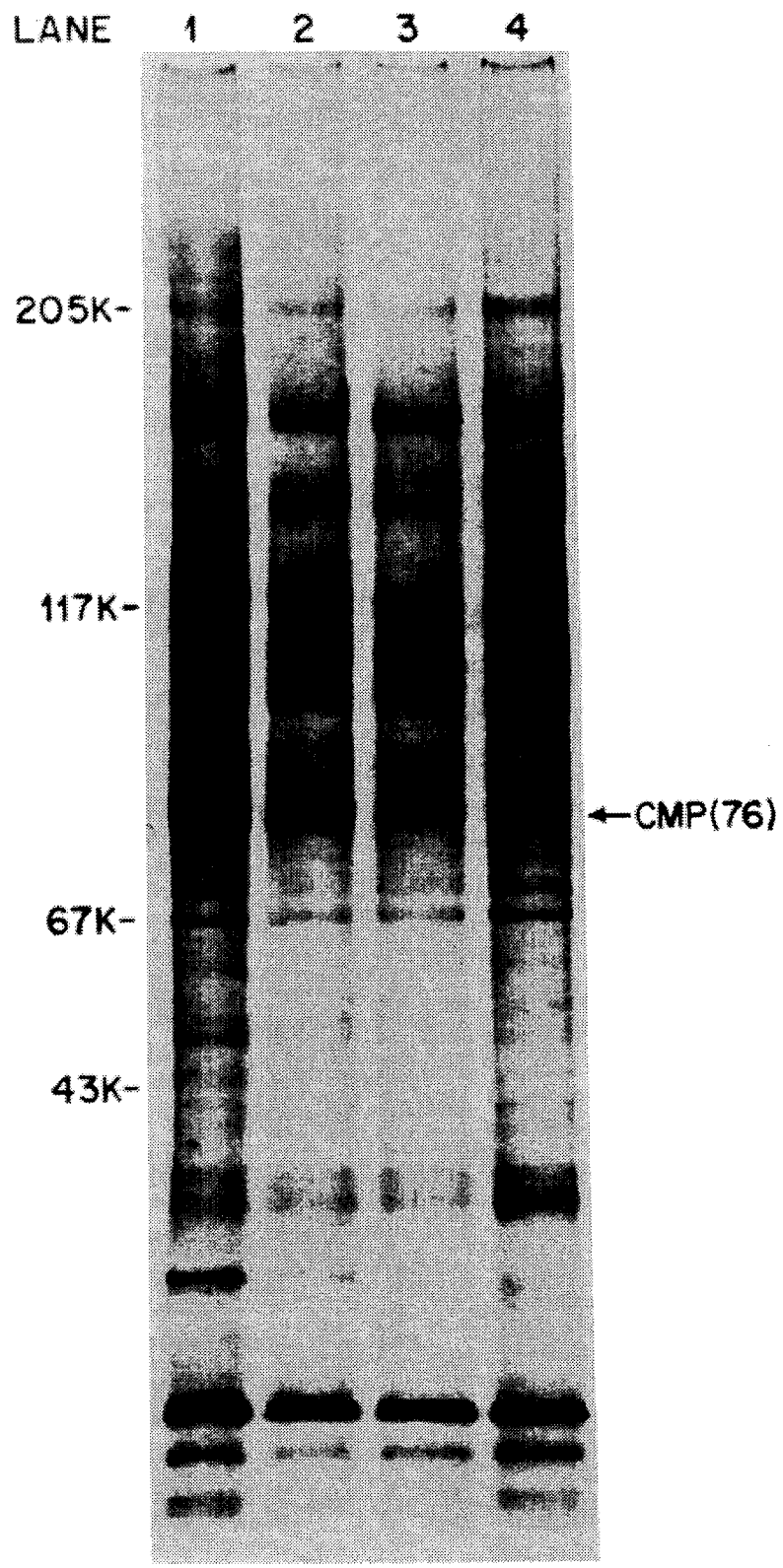
FIG. 1 shows the electrophoresis pattern of concanavalin A-binding glycoproteins.

(1) Purification of CMP
(1) Isolation and culture of chondrocytes

Rabbit chondrocytes were used as the chondrocytes. Rib cartilage growth plates of 4 weeks old New Zealand rabbits were surgically dissected out and then rib cartilage growth plates were treated with trypsin and collagenase according to the method by Kato et al. (op cit.) to isolate chondrocytes. According to this procedure, there were obtained chondrocytes of about $4 \times 10^6$ cells per rabbit. These chondrocytes were sprayed onto culture dishes, each having a culture area of 500 cm$^2$, at about $8 \times 10^5$ cells per dish, 100 ml of DEME medium containing 10% fetal calf serum was added and incubation was carried out at 37° C. under atmosphere of 5% $CO_2$ and 95% air.

(2) Isolation of membrane proteins from chondrocytes

The chondrocytes obtained as described in the above (1) were incubated until they became confluent, the cultured chondrocytes were washed twice with physiological saline as they adhered onto the culture dishes and then the chondrocytes were recovered by means of a scraper. The cells thus recovered were suspended in a four times volume of a cell-disruption buffer (0.25M sucrose, 5mM MOPS/KOH pH 7.4, 1 mM EDTA, 1 mM PMSF, 10µM pepstatin) and the cells were disrupted on ice by means of a homogenizer (available from Polytron Inc.).

The disrupted cell suspension was treated by means of a glass homogenizer using a Teflon rod to disrupt the cell more finely, centrifugation was performed at 4° C. and $105,000 \times$ g for one hour and the supernatant was discarded. The precipitate was resuspended in 24 ml of the same cell-disruption buffer and then cell-disruption was again performed using the glass homogenizer and a Teflon pestle. The cell-disrupted suspension was overlapped on the solutions of sucrose equilibrium density-gradients of 17%/40% previously placed into a centrifuge tube and sedimentation equilibrium centrifugation was performed at 4° C. and $200,000 \times$ g for 1.5 hours. Thereafter, the membrane proteins separated at the interface between 17% sucrose and 40% sucrose were isolated.

(3) Isolation of concanavalin A-binding glycoproteins The above-mentioned membrane fraction was subjected to the following procedure in order to remove the sucrose remaining in the fraction.

The above-mentioned membrane fraction was diluted with a buffer (5 mM MOPS, pH 7.4) and then centrifuged at 4° C. and $100,500 \times$ g for one hour to remove the supernatant. The precipitate was dissolved in a buffer for solubilization (10 mM tris-HCl (pH 7.4), 10 µM APMSF, 10 µM pepstatin) containing 1% deoxycholic acid.

Then, for obtaining the glycoprotein specifically binding concanavalin A, the fractions binding to a wheat germ lectin, was removed from the resultant solution. More specifically, the solution was developed using the wheat germ lectin-WGA-Sepharose 6 MB column (4 cm×2.5 cm, available from Pharmacia AB) previously equilibrated with the buffer for solubilization to recover the non-binding fractions. Thereafter, the fraction not bound to the wheat germ lectin-Sepharose column was developed with the concanavalin A Sepharose column (5 cm×1.5 cm, available from Pharmacia AB) previously equilibrated with the buffer for solubilization, the column was washed with the same buffer as above and the bound glycoproteins were eluted with the same buffer containing 0.5M methyl-α-mannopyranoside.

The eluted fraction was enclosed into a dialysis tube, dialyzed against a dialysis buffer (10mM Tris-HCl, pH 7.4) and then concentrated with an ultrafiltration membrane (available from Centricon-Aminon Inc.).

The concentrated sample was subjected to electrophoresis using 4%/20% gradient gels under a reduced condition according to the method by Lammli. Identification of the proteins were performed with Coomassie Brilliant Blue(CBB) or silver staining. As a result, there was confirmed the presence of 20 or more types of the glycoproteins having different molecular weights.

(4) Extraction of CMP isolated with the gradient gels from the said gels Of the proteins isolated by means of the said electrophoresis, the band having a molecular weight of about 76 kDa was cut out together with the gel thereof in the state of non-CBB staining or silver staining and then the aimed protein was extracted from the gel using an electro-eluter (available from Bio-Rad Laboratories, Inc. U.S.A.).

According to the aforesaid procedure, there were obtained the homogeneous glycoproteins having a molecular weight of about 76 kDa, which was named "chondrocyte membrane protein" abbreviated as CMP.

(5) Enzymatic deglycosilation of CMP For endoglycosidase reactions (C. Maillard et al.; Bone vol. 13, pages 257–264, 1992), purified CMP was incubated with endoglycosidase H (Endo H), endoglycosidase F (Endo F) or N-glycosidase F (NGF) (Boehringer Mannheim Biochemica, Germany). Purified CMP 0.5 µg was incubated with 20 µl of Endo H assay buffer (8 mU Endo H, 50 mM sodium phosphate, pH 5.6, 50 mM EDTA, 0.5 mM PMSF), Endo F assay buffer (40 mU Endo F, 50 mM sodium phosphate, pH 5.6, 50 mM EDTA, 0.5% nonident P40, 0.2% SDS, 1% mercaptoethanol) or NGF assay buffer (5 mU NGF, 45 mM potassium phosphate, pH 7.4, 50 mM EDTA, 0.5% nonident P40, 2% SDS, 1% 2-mercaptoethanol) for 5 hr. or overnight at 37° C. Control incubations were carried out in the absence of enzymes. Samples were boiled for 30 min. Digested protein was analyzed on SDS-PAGE with silver stain to determine molecular weight changes. The results are shown in FIG. 2.

Figure 2:
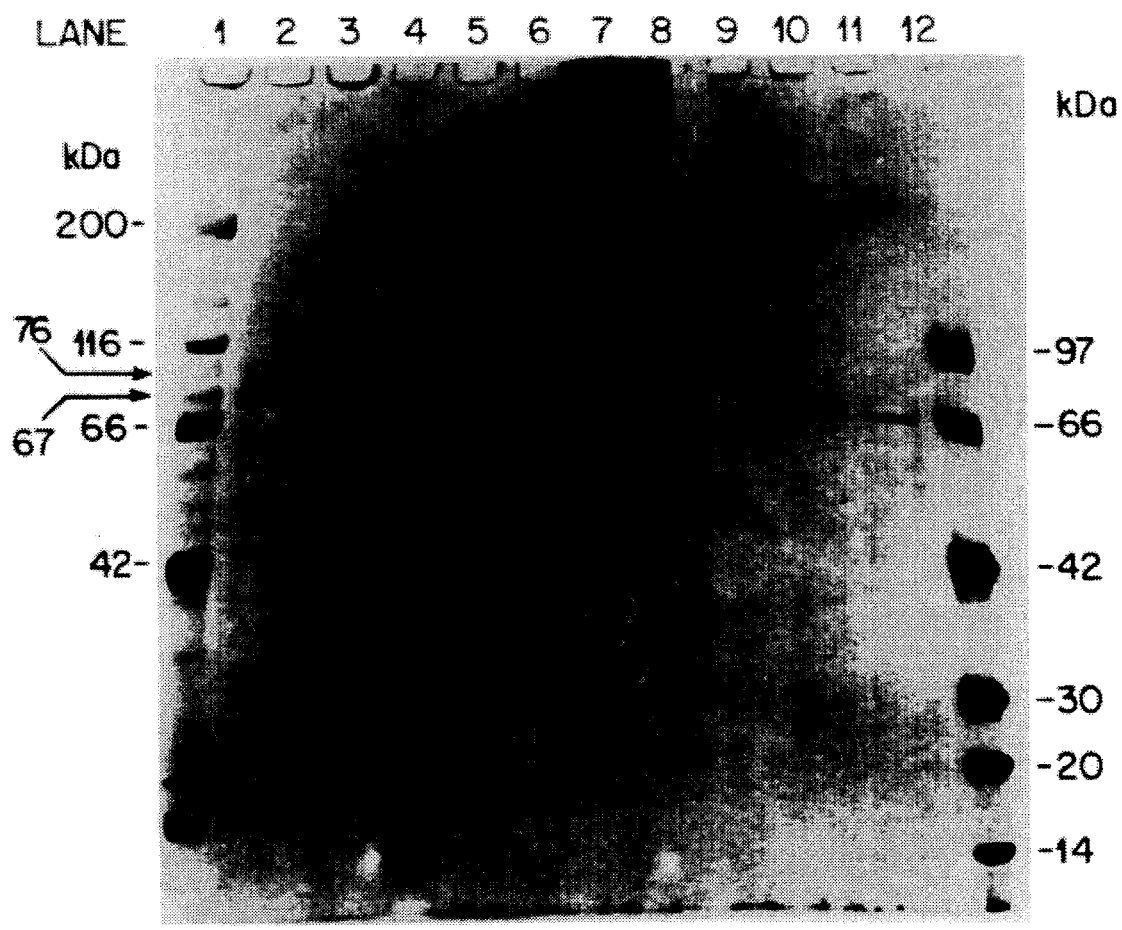
FIG. 2 shows endoglycosidase digestion of purified CMP.

FIG. 2 shows endoglycosidase digestion of purified CMP. Lanes 1 and 12 show high and low molecular markers, respectively. Lane 2 shows the purified CMP. Lanes 3, 6 and 9 show endoglycosidase without CMP. Lanes 4, 7, 10 and 5, 8, 11 show the electrophoresis patterns when CMP was incubated with Endo H, NGF and Endo F for 5 hr. and overnight at 37° C., respectively.

Incubation of CMP with Endo H or NGF resulted in a reduction of the molecular weight of the protein from 76 kDa to 67 kDa, indicating removal of carbohydrate. However, Endo F did not result in molecular weight change of the glycoprotein.

Example 2

(1) Determination of the N-terminal amino acid sequence of CMP The amino acid sequence of N-terminus of CMP was determined according to the following procedure. More specifically, the proteins in the SDS-PAGE gel obtained according to the procedure as described in Example 1 (3) were electrically transcripted onto a PVDE membrane and stained with 1% acetic acid and 0.2% Ponceau S to confirm the band of individual protein and then marked on the membrane. Then, the stained membrane was decolorized with a 0.5 mM sodium hydroxide solution, the CMP-transcripted part of the PVDE membrane was cut out and the N-terminal amino acid sequence was determined by means of an amino acid analyzer (available from Applied Biosystems, Inc., U.S.A.). SEQ ID No. 1 shows the amino acid sequence of N-terminus as determined. In the Sequence, "Xaa" does mean that the amino acid residues were not determined.

(2) Determination of the internal amino acid sequence of CMP The peptide mapping of CMP was performed according to "A Practical Guide To Protein And Peptide Purification For Microsequencing" (Academic Press Inc., 1989). Homogenous CMP (20 μg) was reduced in 50 μl of 8M urea and 0.4M ammonium bicarbonate pH 8.0, containing 45 mM dithiothreitol for 15 rain at 50° C. Carboxymethylation was performed by adding 5 μl of 100 mM iodoacetamide for 15 min at room temperature. 140 μl of water and trypsin (3 mU/mg protein) was added to the reaction mixture. The digestion was allowed to proceed for 24 hr. at 37° C. Peptide mapping was performed on C2/C18 reverse phase column linked to Smart system chromatography (Pharmacia Inc., Sweden). Peptides were eluted with a gradient of 0%–100% solvent B (100% acetonitrile in 0.12% trifluoroacetic acid) over 110 min at a flow rate of 0.1 ml/min. Elution of the peptides from the column was monitored by measuring absorbance at 215 nm. 4 peptide fragments were isolated and named T1, T2, T3 and T4, respectively. Their amino acid sequences were determined by 476A Protein Sequencer (Applied Biosystems, Inc., U.S.A.) and shown in the Sequence listing.

T1 is shown in SEQ ID NO:2; T2 is shown in SEQ ID NO:3; T3 is shown in SEQ ID NO:4; and T4 is shown in SEQ ID NO:5.

Example 3

Comparison of CMP found in chondrocytes and fibroblast-like cells derived by dedifferentiation with a retinoic acid The chondrocytes isolated as described in Example 1 (1) was treated with a retinoic acid to dedifferentiate to fibroblast-like cells. More specifically, to the cultured broth of chondrocytes obtained as described in Example 1(1) was added a retinoic acid in the form of its ethanolic solutions so as to be final concentrations of 0, 0.01 μM, 0.1 μM and 1 μM, respectively, and then the incubation was performed for 96 hours.

The chondrocytes have a weak cell-expanding ability and a spherical shape and, where a retinoic acid is added, they were dedifferentiated to fibroblast-like cells so that they can have an increased expanding ability to take a cellular morphology of being flat and expanded. It may be established upon such morphological changes whether or not dedifferentiation might be performed, and the dedifferentiation was also confirmed by this experiment. Also, it was confirmed that the dedifferentiation level may depend upon the concentration of a retinoic acid and the period of time for treatment.

On each of the chondrocytes incubated with the various concentrations of a retinoic acid added as described above, cells were recovered according to the procedure as described in Example 1 (2) to obtain membrane proteins. Then, the concanavalin A-binding glycoprotein fraction was obtained according to the procedure as described in Example 1 (3) and its electrophoresis pattern was compared using SDS-PAGE. The results are shown in FIG. 1.

FIG. 1 shows a comparison of CMP's found in chondrocytes and fibroblast-like cells derived by dedifferentiation. Lane 1shows the electrophoresis pattern when no retinoic acid was added, and Lanes 2, 3 and 4 show the electrophoresis patterns when a retinoic acid was added to the medium at final concentrations of 0.01 μM, 0.1 μM and 1 μM, respectively. Molecular weights are shown on the left side of Lanes, while the location of CMP is shown on the right side of Lanes together with its molecular weight.

Thus, it was confirmed that CMP disappeared depending upon the concentrations of a retinoic acid added. CMP disappeared together with dedifferentiation, namely, dedifferentiation to fibroblast-like cells.

Example 4

Preparation of anti-CMP antiserum

The gel band containing CMP obtained as described in Example 1 (4) was cut out together with its gel portion, homogenized and subcutaneously administered to mice. At 3 weeks after the administration, partial blood samples were collected to confirm a sufficiently high level of the antibody valence to CMP and then the serum was collected to obtain anti-CMP antiserum.

Example 5

Confirmation test for the presence of CMP in various organs

The specific expression of CMP in chondrocytes was further investigated using various organs or cells according to Western blot technique with the anti-CMP antiserum obtained as described in Example 4.

More specifically, the membrane proteins were obtained from 6 types of rabbit organs; kidney, liver, brain, testis, intestine and spleen, and rabbit cultured fibroblasts, respectively according to the procedure as described in Example 1 (2). The membrane proteins above were individually investigated for the presence or absence of CMP according to Western blot technique to confirm that CMP is not found in all fractions, which proved that CMP is a protein specifically expressed in chondrocytes.

What is claimed is:

1. A chrondrocyte membrane protein (CMP) with a molecular weight of about 76 kD or of about 67 kD after treatment with endoglycosidase as analyzed by sodium dodecyl sulfate-polyacrylamide gel electrophoresis SDS-PAGE.

2. The protein as claimed in claim 1 comprising at least one of the amino acid sequences as shown in SEQ ID NO:1, SEQ ID NO:2, SEQ ID No:3, SEQ ID NO:4, or SEQ ID NO:5.

3. A pharmaceutical containing CMP according to claim 1.

4. A diagnostic aid containing CMP according to claim 1.

5. A CMP, as claimed in claim 1, obtainable by a process comprising
   (a) isolating chondrocytes;
   (b) separating membrane proteins from the chondrocytes of step (a);
   (c) isolating concanavalin A-binding glycoproteins through a concanavalin A-affinity column; and
   (d) isolating CMP.

6. A CMP according to claim 5, wherein the process further comprises, prior to step (c), separating concanavalin A-binding glycoproteins from other membrane proteins.

7. A method for the isolation of CMP comprising the following steps:
   (a) isolating chondrocytes;
   (b) separating membrane proteins from the chondrocytes of step (a);
   (c) isolating concanavalin A-binding glycoproteins through a concanavalin A-affinity column; and
   (d) isolating CMP.

8. A method according to claim 7, further comprising, prior to step (c), separating concanavalin A-binding glycoproteins from other membrane proteins.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 6..7
    ( D ) OTHER INFORMATION: /note="Xaa is an unknown amino acid."

( x i ) SEQUENCE DESCRIPTION: SEQ ID NO:1:

Ser Val Glu Val Arg Xaa Xaa Thr Ala Ser Glu Pro Pro Gln Gln
  1               5                   10                  15

( 2 ) INFORMATION FOR SEQ ID NO:2:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 16
    ( D ) OTHER INFORMATION: /note="Xaa is an unknown amino acid."

( x i ) SEQUENCE DESCRIPTION: SEQ ID NO:2:

His Thr Thr Tyr Phe Asp Asn Thr Asn Gly His Asn Pro Glu Pro Xaa
  1               5                   10                  15
  Ala Ala ( 2 ) INFORMATION FOR SEQ ID NO:3:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

Thr Val Gly Trp Asn Val Pro Val Gly Tyr Leu Val Asp Ser Gly Arg
  1               5                   10                  15

( 2 ) INFORMATION FOR SEQ ID NO:4:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 18
    ( D ) OTHER INFORMATION: /note="Xaa is an unknown amino -continued acid."

( x i ) SEQUENCE DESCRIPTION: SEQ ID NO:4:

```
Thr Thr Tyr Gln Asp Thr Leu Gly Pro Asp Tyr Val Ala Ala Leu Glu
1               5                   10                  15

Gly Xaa Gln Ser
            20
```

( 2 ) INFORMATION FOR SEQ ID NO:5:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:5:

```
Tyr Tyr Asp Tyr Ser Gly Ala Phe Arg
1               5
```